United States Patent [19]
Fanger et al.

[11] Patent Number: 6,096,311
[45] Date of Patent: *Aug. 1, 2000

[54] METHODS FOR USE OF MONOCLONAL ANTIBODIES SPECIFIC FOR THE HIGH AFFINITY FC RECEPTOR FOR IMMUNOGLOBULIN G

[75] Inventors: Michael W. Fanger, Lebanon; Paul M. Guyre, Hanover, both of N.H.; Clark L. Anderson, Columbus, Ohio

[73] Assignee: Medarex, Annandale, N.J.

[ * ] Notice: This patent is subject to a terminal disclaimer.

[21] Appl. No.: 08/866,982

[22] Filed: Jun. 2, 1997

Related U.S. Application Data

[63] Continuation of application No. 08/364,435, Dec. 27, 1994, Pat. No. 5,635,600, which is a continuation of application No. 08/237,313, May 3, 1994, abandoned, which is a continuation of application No. 07/933,874, Aug. 21, 1992, abandoned, which is a continuation of application No. 07/151,450, Feb. 2, 1988, abandoned, which is a continuation-in-part of application No. 07/069,412, Jul. 1, 1987, Pat. No. 4,954,617, which is a continuation-in-part of application No. 06/882,181, Jul. 7, 1986, abandoned.

[51] Int. Cl.[7] .......................... A61K 39/395; C12P 21/08; C12K 16/00
[52] U.S. Cl. ..................... 424/136.1; 424/143.1; 424/152.1; 424/155.1; 424/172.1; 424/174.1; 424/138.1; 530/387.3; 530/388.2; 530/388.22; 530/388.25; 530/388.7
[58] Field of Search .............. 424/136.1, 138.1, 424/141.1, 152.1, 155.1, 147.1, 160.1, 172.1, 174.1, 143.1; 530/387.3, 388.2, 388.22, 388.25, 388.7

[56] References Cited

PUBLICATIONS

Waldmann (Science, 252:1657–1662), 1991.
Hird (in Genes and Cancer, Carney and Sikora, eds, John Wiley & Sons, Chichester, pp. 183–189), 1990.
Harris et al (TIBTECH, 11;42–44), 1993.
Kimmel et al (J. Neurosurg., 66:161–171), 1987.
Kahan (Cur. Opin. Immunol., 4:553–560), 1992.
Bach (TIPS, 14:213–216), 1993.
Fahey et al (Clin. Exp. Immunol., 88:1–5), 1992.
Schlom (in Broder, Molecular Foundations of Biology, Williams & Wilkins, Baltimore pp. 95–134), 1991.
Burmester et al (Baillieres Clinical Rheumatology, 6:415–434), 1992.

*Primary Examiner*—Paula K. Hutzell
*Assistant Examiner*—Susan Ungar
*Attorney, Agent, or Firm*—Lahive & Cockfield, LLP; Jane E. Remillard; Giulio A. DeConti, Jr.

[57] ABSTRACT

Monoclonal antibodies which react specifically to Fc receptor of human effector cells are disclosed. Binding of the antibodies to the receptor is not blocked by human immunoglobulin G. The antibodies are useful for targeting human effector cells (e.g. macrophages) against a target cell (e.g. a cancer cell, an infectious agent, etc.) For this purpose, bifunctional antibodies or heteroantibodies can be constructed containing the binding region derived from an anti-Fc receptor antibody and the binding region of a target-specific antibody. Targeted effector cells can be used to kill target cells by cell mediated antibody dependent cytolysis.

6 Claims, 8 Drawing Sheets

| Lane | Preclearing Adsorbant | Final Adsorbant | Band Density | % Depletion |
|---|---|---|---|---|
| 1 | mIgG1 | mIgG2a | 310 | --- |
| 2 | mIgG1 | 32 | 217 | --- |
| 3 | mIgG2a | 32 | 23 | 89 |
| 4 | 32 | mIgG2a | 85 | 73 |
| 5 | 32 | 32 | 42 | 81 |
| 6 | mIgG2a | mIgG2a | 23 | 93 |

Fig. 2

METHODS FOR USE OF MONOCLONAL ANTIBODIES SPECIFIC FOR THE HIGH AFFINITY FC RECEPTOR FOR IMMUNOGLOBULIN G

RELATED APPLICATIONS

This application is a continuation application of Ser. No. 08/364,435 entitled "Specific Antibodies and Heteroantibodies Specific for the High Affinity Fc Receptor for Immunoglobulin G on Human Mononuclear Phagocytes" (amended title) filed on Dec. 27, 1994, issued on Jun. 3, 1997 as U.S. Pat. No. 5,635,600, which in turn is a continuation application of Ser. No. 08/237,313 entitled "Monoclonal Antibodies to Fc Receptors for Immunoglobulin G on Human Mononuclear Phagocytes" filed on May 3, 1994, abandoned, which in turn is a continuation application of Ser. No. 07/933,874 entitled "Monoclonal Antibodies to Fc Receptors for Immunoglobulin G on Human Mononuclear Phagocytes" filed on Aug. 21, 1992, abandoned, which in turn is a continuation application of Ser. No. 07/151,450 entitled "Monoclonal Antibodies to Fc Receptors for Immunoglobulin G on Human Mononuclear Phagocytes" filed on Feb. 2, 1988, abandoned, which in turn is a continuation-in-part of Ser. No. 07/069,412 entitled "Monoclonal Antibodies to Fc Receptors for Immunoglobulin G on Human Mononuclear Phagocytes" filed on Jul. 1, 1987, issued as U.S. Pat. No. 4,954,617, and which in turn is a continuation-in-part of Ser. No. 06/882,181 filed on Jul. 7, 1986, abandoned. The contents of all of the aforementioned application(s) are hereby incorporated by reference.

GOVERNMENT SUPPORT

The work described herein was supported by one or more grants from the Department of Health and Human Services.

BACKGROUND

Several types of effector cells have surface receptors that bind the Fc portion of immunoglobulin (IgG). When such cells (monocytes, granulocytes, K cells, etc.) encounter target cells that have been opsonized with IgG antibodies, they form conjugates with the target cells. Subsequently, the effector cells either lyse or phagocytose the target cells, depending upon the effector cell type, the target cell type and the specific Fc receptor type involved.

Two distinct classes of IgG Fc receptors (FcR) have been identified on human monocytes and on the human monocytic cell line U937. Looney, R. J., et al., (1986) *J. Immunol.* 136:1641–1647. One is a 72 kDa sialoglycoprotein (p72) with high affinity ($K_a=10^8-10^9$ M-1) for monomeric human IgG1 and IgG3 and for murine subclasses IgG2a and IgG3. Alexander, M. D., et al. (1978) *Immunol.* 35:115–123; Anderson, C. L. and Abraham, G. N. (1980) *J. Immunol.* 125:2735–2741; Lubeck, M. D. et al. (1985) *J. Immuno.* 135: 1299–1304. The other receptor is a 40 kDa molecule (p40) which shows relatively low affinity for monomeric IgG. Looney, et al., supra; Jones, D. H., et al. (1985) *J. Immunol.* 135:33483353. P40 has been defined by its ability both to form rosettes with erythrocytes coated with murine IgG1 and to bind aggregated murine IgG2b at low ionic strength. In addition, a monoclonal antibody (IV3) has been prepared which binds to the 40 kDa receptor and inhibits ligand binding. See Looney, R. J., et al., supra. This receptor is present not only on mononuclear phagocytes but on human platelets, neutrophils and eosinophils. Rosenfeld, S. I., et al. (1985) *J. Clin. Invest.* 76:2317–2322.

These two Fc receptors on human monocytes have been shown to mediate anti-T3-induced human T cell mitogenesis by distinct subclasses of murine IgG. The 72 kDa FcR mediates murine IgG2a anti-T3-induced stimulation whereas the 40 kDa FcR mediates murine IgG1 anti-T3-induced T cell mitogenesis. See Looney et al., supra. Based upon their distinctive affinities for murine IgG subclasses, p72 and p40 are thought to be the human homologues of murine macrophage FcRI and FcRII specific for murine IgG2a and IgG2b/1, respectively. Although not present on monocytes or U937 cells, a third class of IgG FcRs has been described on human neutrophils and null cells.

It has been demonstrated that target cell conjugation and lysis can also be induced by covalently cross-linked heteroantibody made up of both anti-Fc receptor antibody and antibody directed against a target cell epitope. When effector cells bind such heteroaggregates to their Fc receptor, they can specifically bind and lyse target cells which have not been opsonized, but which express the appropriate target antigen. Segal et al. have recently reported cytolysis of tumor cells by mouse monocytes with an attached heteroantibody which joins the Fc receptor of the monocyte on one end with tumor cell epitopes on the other end. The targeting of effector cells with conventional heteroantibodies, however, is likely to be only marginally effective in vivo because the binding of antibody to Fc receptors can be blocked by physiological concentrations of IgG.

DISCLOSURE OF THE INVENTION

This invention pertains to monoclonal antibodies which are specific for the human high affinity Fc receptor for IgG, the p72 receptor, and which bind to the Fc receptor without being blocked by human IgG. The antibodies bind specifically, through their antigen combining region and independent of their Fc portion, to human receptor for the Fc portion of IgG. The antibodies bind to a site on the Fc receptor distinct from the binding site for the Fc region of IgG (ligand) and the antibodies are capable of binding a ligand-occupied receptor.

The anti-Fc receptor antibody of this invention can be made by monoclonal antibody producing techniques. Fc receptor protein can be obtained for immunization by preparing a cell fraction containing Fc receptor from a cell line that expresses Fc receptor (e.g. the U937 line, a human monocytic cell line that expresses Fc receptor for human IgG). The cells can be pretreated in culture with IFN-gamma to enhance the yield of Fc receptor protein. Fc receptor protein is purified by affinity purification from cell lysates. An animal is immunized with the purified receptor protein and antibody-producing cells are harvested from the animal and fused with a myeloma cell or other immortalizing cell to produce hybridomas. The hybridomas are cloned and clones are selected for production of antibody to Fc receptor which is not blocked by human IgG.

The selection of antibody which binds to the Fc receptor through its antigen binding region (distinct from the Fc portion of the antibody) is complicated by the fact that the Fc portion of IgG of the animal species may bind human Fc receptor. For example, two of the four murine IgG subclasses—IgG2a and IgG3—bind to the high affinity human Fc receptor via their Fc portion. In such instances selection can be facilitated as follows: After initial screening of hybridomas for production of Ig which binds the receptor, hybridomas which produce antibody of the subclass which is bound via its Fc region by the human Fc receptor, are eliminated from consideration. The remaining hybridomas are evaluated for production of antibody which binds Fc receptor independently of their Fc portion.

The anti-Fc receptor antibody of this invention can be used to produce target-specific effector cells for treatment of cancer, allergies, and infectious and autoimmune diseases. Antibody specific for a target cell (targeting antibody) can be linked to the Fc receptor of effector cell through the Fc-specific antibody of this invention. The linkage mediated by this anti-Fc receptor antibody is not disruptable by IgG because binding to the receptor does not involve the Fc portion of the antibody.

For the purpose of targeting effector cells, a bifunctional antibody (used herein to mean a single antibody or antibody fragment with a dual binding specificity) or a heteroantibody (used herein to mean an aggregate of two or more antibodies (or antibody fragments) each antibody having a different specificity) can be produced. In general, the bifunctional antibody or heterantibody comprises:

a. at least one antigen binding region derived from an anti-Fc receptor antibody whose binding to human Fc receptor is not blocked by human immunoglobulin G; and b. at least one antigen binding region specific for a target cell.

The binding of bifunctional or heteroantibody to the effector cell results in a targeted effector cell i.e., an effector cell with attached bifunctional or heteroantibody containing antigen binding regions which are specific for a desired target cell. The targeted effector cells can be used to bring about antibody dependent cell mediated cytolysis (ADCC) of the target cells in vivo.

The target cell can be a cancer cell or other cell whose elimination would be beneficial to the host, for example, an auto-antibody producing cell found in autoimmune diseases, or an IgE producing cell found in allergies. The target cell specificity of the bifunctional antibody or the heteroantibody is derived from a targeting antibody i.e., an antibody specific for a target cell-associated or target cell-specific antigen. The use of the Fc specific antibody of this invention provides for attachment of the targeting antibody to monocyte effector cells by a linkage which is not disrupted by physiological levels of immunoglobulin G encountered in vivo. Thus, the targeted effector cells can be given in vivo without loss of effector cell specificity due to IgG competition for Fc receptor sites.

The anti-FcRI antibody of this invention has other therapuetic applications as well as several diagnostic applications. The antibody can be used as a targeting antibody to target FcRI-bearing cells. The antibody can also be used to induce capping and removal of Fc receptors on monocyte or other cells. Diagnostic applications of the antibodies include their use in assays for FCRI receptor levels and assays for substances that influence FcRI receptor levels.

DESCRIPTION OF THE FIGURES

FIG. 2 shows SDS-PAGE analysis of affinity adsorption with ligand or with mab 32 after pre-clearing U937 lysates with ligand or with mab 32.

DETAILED DESCRIPTION OF THE INVENTION

Figure 1:
FIG. 1 shows SDS-PAGE of affinity adsorbed lysates of surface radioiodinated U937 cells.

The antibody of this invention binds the high -affinity (p72) Fc receptor (FcRI) for human IgG without being blocked by human IgG. Preferred anti-FcRI receptor antibody has the following characteristics:

a. the antibody reacts specifically with the high affinity Fc receptor;

b. the antibody reacts with the receptor through its antigen combining region independent of its Fc portion;

c. the antibody reacts with an epitope of FcRI which is distinct from the Fc (or ligand binding) site of the receptor; and d. the antibody binds ligand (Fc) occupied receptor.

The monoclonal anti-Fc receptor antibody of this invention can be produced by conventional monoclonal antibody methodology e.g., the standard somatic cell hybridization technique of Kohler and Milstein, *Nature* 256: 495 (1975). Although somatic cell hybridization procedures are preferred, in principle, other techniques for producing monoclonal antibody can be employed e.g., viral or oncogenic transformation of B lymphocytes.

Fc receptor for immunization of an animal can be prepared from lysates of human cells which express the receptor. A preferred receptor-bearing cell line is the human monocytic cell line U937; however, other monocytic cells such as HL-60 cells or freshly isolated monocytes can be used. Because interferon-gamma enhances Fc receptor expression, the cells can be cultured in the presence of interferon-gamma (e.g. 100 IU/ml) before receptor preparation to enhance the yield of receptor protein.

A partially purified preparation of the receptor can be made by lysing receptor-bearing cells and then purifying the receptor by immuno-adsorbant chromatography. Cells can be lysed in a buffer containing a detergent such as NP40. The immuno-adsorbent can be prepared by attaching human IgG to a water-insoluble material such as an activated Sepharose™ resin. The Sepharose resin with attached human IgG is poured into a column. The cell lysate is passed through the column under conditions which permit adsorbtion of the cellular Fc receptor protein by the IgG coupled to the resin. The adsorbed Fc receptor protein can be eluted with a mildly acidic elution buffer. The purified receptor can then be used for immunization of an animal to produce anti-receptor monoclonal antibody.

As an alternative to the use of partially purified receptor protein, whole FcRI-bearing cells can be used as immunogen. For example, whole interferon-gamma treated U937 cells can be used to elicit anti-FcRI antibody.

The preferred animal system for preparing hybridomas is the murine system. Hybridoma production in the mouse is a very well-established procedure. Immunization protocols and techniques for isolation of immunized splenocytes for fusion are well known in the art. Fusion partners (e.g., murine myeloma cells) and fusion procedures are also well-known.

Selection of murine hybridomas producing antibody against the FcRI for IgG of human monocytes, however, is complicated by the fact that two subclasses of murine IgG—the IgG2a and IgG3 subclasses—are ligands capable of binding with high affinity to this receptor. Thus, assays for monoclonal antibody capable of binding to the receptor would register as positive all murine antibodies of these two subclasses. This obstacle can be avoided by first screening hybrid cells for production of antibody reactive with the cell line which was the source of Fc receptor, then eliminating hybrid cells which produce IgG2a and IgG3 antibodies and finally, evaluating remaining hybridomas for production of antibody against high affinity receptor. This strategy is further detailed in the exemplification below.

Employing the methodology described, five murine monoclonal anti-FcRI antibodies were prepared. The antibodies are designated mab 22, mab 32, mab 44, mab 62 and mab 197. A hybridoma cell line producing mab 22 was deposited with the American Type Tissue Culture Collection (ATCC), Rockville, Md. 20852 on Jul. 9, 1996 and has been assigned ATCC Designation No. 11B-12147. Each of the antibodies exhibit the preferred characteristics set forth above.

The anti-Fc receptor antibody of this invention can be used to produce target-specific effector cells i.e. effector cells which are capable of recognizing and binding to a target cell and exerting their effector function. It provides a means for attaching to an effector cell an antibody or antibody-binding fragment directed against a target cell. The attachment is not disruptable by physiological concentrations of IgG because the anti-Fc antibody which mediates the attachment binds the receptor through its antigen-binding region. Effector cells, such as macrophages, targeted in this way can be employed to bring about antibody-dependent cell-mediated killing of target cells.

To target effector cells, bifunctional antibodies or heteroantibodies are employed. These antibodies have dual antigen binding specificity—one specificity for the Fc receptor (preferably the high affinity Fc receptor) and one specificity for an epitope of the target cell. The Fc receptor specificity mediates linkage to the effector cell through a known cytotoxic trigger molecule. The target cell specificity provides for recognition and binding to the target cell.

Bifunctional antibodies are single, divalent antibodies which have two different antigen binding sites. Bifunctional antibodies for targeting have one binding site for Fc receptor and one binding site for a target cell epitope.

Hetereoantibodies are two or more antibodies or antibody binding fragments (Fab) linked together, each antibody or fragment having a different specificity. Heteroantibodies for targeting comprise an antibody (or antigen binding fragment specific for Fc receptor, coupled to an antibody (or antigen binding fragment thereof) specific for a target cell epitope.

Bifunctional antibodies can be produced by chemical techniques (see e.g., D. M. Kranz et al., *Proc. Natl. Acad. Sci. USA* 78,5807 (1981)) by "polydoma" techniques (See U.S. Pat. No. 4,474,893, to Reading) or by recombinant DNA techniques. Heteroantibodies can be prepared by conjugating Fc receptor antibody with antibody specific for an epitope of a target cell. A variety of coupling or cross-linking agents can be used to conjugate the antibodies. Examples are protein A, carboiimide, and N-succinimidyl-3-(2-pyridyldithio) propionate (SPDP). SPDP is the preferred agent; procedures for crosslinking antibodies with this agent are known in the art. See e.g., Karpovsky et al., (1984) *J. Exp. Med.* 160:1686; Liu, M. A. et al., (1985) *Proc. Natl. Acad. Sci USA* 82:8648.

Target cells are cells whose elimination would be beneficial to the host. One important type of cell is a tumor cell. Effector cells can be targeted with bifunctional or heteroantibody having specificity for FcRI and specificity for a tumor associated or tumor specific antigen.

Antibodies with a desired tumor specificity for production of bifunctional antibody or hetero-antibody can be produced or can be selected from available sources. Monoclonal antibodies against tumor-associated antigens can be made by the methods of Koprowski et al., U.S. Pat. No. 4,172,124. Many suitable anti-cancer antibodies are presently available.

Specific anti-tumor antibodies would include, but not be limited to:

| Antibody | Specificity |
| --- | --- |
| AML-2-23, PM-81, PMN-6, PMN-19 | Myeloid Leukemia |
| SCCL-1, SCCL-175 | Small Cell Carcinoma of the Lung |
| OC1-25, OVCT-3 | Ovarian Carcinoma |
| COL-1, COL-2, COL-3, . . . COL-13 | Colon Carcinoma |

In addition to tumor cells, the effector cell can be targeted against auto-antibody producing lymphocyte for treatment of autoimmune disease or an IgE-producing lymphocyte for treatment of allergy. The target can also be microorganism (bacterium or virus) or a soluble antigen (such as rheumatoid factor or other auto-antibodies).

Effector cells for targeting are human leukocytes, preferably macrophages. Other cells would include monocytes, IFN-gamma activated neutrophils, and possibly IFN-gamma activated natural killer (NK) cells and eosinophils. Macrophages can be treated with IFN-gamma before targeting, to increase the number of Fc receptors for attachment of the targeting antibody or heteroantibody. The effector cells may also be activated before targeting by other cytokines such as tumor necrosis factor, lymphotoxin, colony stimulating factor, and interleukin-2. If desired, effector cells for targeting can be obtained from the host to be treated.

The targeted effector cells can be administered as a suspension of cells in a physiologically acceptable solution. The number of cells administered can be in the order of $10^8$–$10^9$ but will vary depending on the therapeutic purpose. In general, the amount will be sufficient to obtain localization at the target cell and to effect target cell killing by antibody dependent mediated cytolysis (ADCC). Routes of administration can also vary. In tumor therapy, for instance, depending upon the localization of a tumor, the targeted effector cells could be administered intravenously, or directly into tumor sites; as for example, directly into the peritoneal cavity in the case of ovarian carcinoma.

Therapy with targeted effector cells can be performed in conjunction with other techniques for removal of targeted cells. For example, anti-tumor therapy with effector cells armed with FcRI/antitumor antibody can be used in conjunction with surgery, chemotherapy or radiotherapy.

Additionally, combination immunotherapy may be used to direct two distinct cytotoxic effector populations toward tumor cell rejection. For example, antitumor antibodies linked to anti-T3 that will trigger cytolytic T lymphocytes to lyse tumor cells may be used in conjunction with anti-RcRI antitumor hetero-antibodies. Protocols based on these concepts may be especially effective in removing residual tumor cells in patients induced into remission by chemotherapy and irradiation.

The anti-Fc receptor antibody of this invention has additional utility in therapy and diagnosis. The Fc receptor antibody itself can be a targeting antibody (i.e., to target for cells bearing FcRI receptor). The antibody can be used to target lipid vesicles containing anticancer drugs for treatment of certain hematological cancers (e.g. acute myeloid leukemia), or to target lipid vesicles containing factors (such as gamma-IFN) which activate monocytes. The antibody, if of the appropriate murine IgG subclass (e.g., IgG2a), can be used directly in vivo to eliminate Fc receptor bearing cells (e.g., myeloid leukemia cells) via natural complement or ADCC mechanisms.

Moreover, immunotoxins can be prepared that are conjugates of an anti-Fc receptor antibody and a toxin such as ricin, diphtheria toxin or Pseudomonas exotoxin or subunits of these toxins. studies on the preparation, antitumor effects and pharmokinetics of immunotoxins (See E. Vitetta et al., *Science*, 238, 1098–1104 (1987)) as well as clinical trials (see L. Spitlet, *Clin. Chemistry*, 33(b), 1054 (1987)) have been performed.

Unlike many immunotoxins that localize toxic compounds merely at the cell surface, the immunotoxins of this invention rely on the critical role of the high affinity Fc receptor for IgG in mediating uptake of antibody into the Fc receptor-bearing cell. Immunotoxins made with the antibodies of this invention then, will be internalized by FcR-bearing cells. Immunotoxins prepared using Mab's of this invention that recognize high affinity Fc receptors (e.g., Mab 22, Mab 32, Mab 44, Mab 62 or Mab 197) can be more efficient than other immunotoxins that are not internalized. The immunotoxins of this invention can be directed towards cells that express high affinity Fc receptors, especially cancer cells which bear the receptor. For example, myeloid leukemia cells express the high affinity Fc receptors and the numbers of the receptor can be increased with IFN-gamma. The monoclonal antibody 197 has been shown to be rapidly internalized by a myeloid leukemia cell line after binding to the Fc receptor. Immunotoxins prepared with the monoclonal antibody of this invention can be more efficacious than immunotoxins directed toward other myeloid surface antigens which are not internalized.

The anti-FcR antibody of this invention can be employed to modulate Fc receptor levels on monocytic cells. For example, in auto-immune diseases (such as rheumatoid arthritis) the antibody can be administered in a form that induces "capping" and elimination of Fc receptors on the cell surface. The reduction of Fc receptors can interfere with monocyte clearance of antibody coated self-cells in patients. Mixtures of anti-Fc receptor antibodies can also be used for this purpose.

Diagnostic applications of the anti-FcR antibody of the invention can be based on the use of the antibody to quantify the distribution or number of Fc receptors on cells. The antibody can be employed in assays for agents which influence receptor expression (e.g., interferon-gamma, which enhances Fc receptor expression). For example, in an assay for interferon-gamma the anti-FcRI antibody labeled (radioisotopically, enzymatically or fluorescently) can be used to quantify FcRI levels on cells exposed to a test sample. Receptor levels will be related to the amount of interferon-gamma in the sample.

The antibody can also be used to subclassify patients with rheumatologic disorders which are related to Fc receptor levels or to the ability of a patient's cells to respond to interferon by enhanced expansion of Fc receptors.

Based on the increased expression of FcRI on IFN-gamma plus dexamethasone-treated monocytes it is anticipated that anti-FcRI monoclonal antibodies will be excellent markers of inflammatory macrophages. It is possible that the accumulation and activation of mononuclear phagocytes at sites of inflammation (including but not limited to infectious foci, septic arthritis, atherosclerotic plagues) can be detected by radio-imaging using radiolabelled antibodies to the FCRI on such cells.

In vivo radioimaging methods of this invention involve the administration of monoclonal anti-FcRI antibodies or fragments thereof (e.g., Fab, F(ab')$_2$) that have been labeled with a radioisotope detectable by an external photoscanning device. Preferred labels are gamma-emitting radioactive metals such as Technetium-99m, Indium-111, and Gallium-67 which are detectable with a gamma camera. The labeled anti-Fc receptor antibody (or fragment) is administered (generally intraveneously) and allowed to localize to Fc receptor-bearing cells. The localized antibody is imaged using appropriate photoscanning procedures.

The invention is illustrated further by the following exemplication:

EXEMPLIFICATION

Materials and Methods

Chemical and Reagents

Cytochrome c Type VI, superoxide dismutase, pepstatin, chymostatin, leupeptin, antipain, rabbit muscle actin and phenylmethylsulfonylfluoride (PMSF) were purchased from Sigma Chemical Co., St. Louis, Mo.; Dextran T500, Ficoll-Hypaque, Sepharose 4B, CNBr-activated Sepharose, Protein A-Sepharose CL-4B from Pharmacia Fine Chemicals, Piscataway, N.J.; tetanus toxin, octyl-b-D-glucopyranoside (octylglucoside) and papain from Calbiochem, La Jolla, Calif.; human anti-tetanus toxin antibody (HyperTet™) from Cutter Laboratories, Berkeley, Calif.; chloroglycouril from Pierce Chemical Co., Rockford, Ill.; carrier-free I$^{125}$ (IMS.300) from Amersham, Arlington Heights, Ill.; cytochalasin B from Aldrich Chemical Co., Milwaukee, Wis.; goat F(ab')2 antimurine Ig (anti-mIg), both fluorescein isothiocyanate-conjugated (FITC) and unconjugated, from Cappel, West Chester, Pa., unless indicated otherwise; RPMI 1640 from Gibco, Grand Island, N.Y., and from K C Biologicals, Lenexa, Kans.; Fetal bovine serum (FBS) from Sterile Systems, Logan Utah; and a mixture of low molecular weight markers from Biorad, Richmond, Calif. Recombinant gamma interferon was kindly donated by Genentech, South San Francisco, Calif. 1,25-dihydroxycholecalciferol (1,25(OH)$_2$D$_3$) was a gift from Hoffman LaRoche, Nutley, N.J. Other chemicals were of analytical grade and were obtained commerically.

NP40 lysis buffer contained 1% NP40, 110 mM NaCl, 10 mM EDTA, 2 mM PMSF, 10 ug/ml pepstatin, 10 ug/ml chymostatin, 10 ug/ml leupeptin and 10 ug/ml antipain in 20 mM Tris buffer, pH 7.1. Krebs Ringer phosphate buffer with glucose (KRPglu) consisted of 135 mM NaCl, 5 mM KCl, 1.2 mM MgSO4, 1 mM CaCl$_2$, 4.3 mM glucose in 10 mM sodium phosphate buffer, pH 7.4. Phosphate buffered saline (PBS) was 145 mM NaCl in 20 mM phosphate buffer, pH 7.0. PBS-K contained 130 mM NaCl and 5 mM KCl in 10 mM phosphate buffer, pH 7.4.

Antibodies

The monoclonal antibody against the high affinity FcR (herein designated mab 32 and when subcloned, 32.2), was prepared as follows: A partially purified detergent lysate of the high affinity FcR from U937 cells was obtained in a manner similar to a published method (See Anderson, C. K., et al., (1984) *J. Immunol.* 134:465–470). U937 cells were lysed in 1% NP40 and the lysate was allowed to incubate with Sepharose hIgG for 8 hours. The adsorbent was washed thoroughly and was eluted with 0.5 M acetic acid in 30 mM octylglucoside. The eluate was promptly neutralized with 2 M Tris and the amount of protein eluted was determined by a Folin assay (Peterson, G. L. (1977) *Anal. Biochem.* 85: 346–356). The tubes containing the bulk of the protein were pooled, concentrated by vacuum dialysis using an Amicon YM-10 filter and a Minicon apparatus to 0.5 ml and emulsified with an equal volume of Freund's adjuvant, either complete for the first injection or incomplete for subsequent ones. A mouse was immunized intraperitoneally 4 times at roughly 4 week intervals, the last 2 immunizations using antigen derived from U937 cells cultured 72 hours in IFN-gamma, 100 IRU/ml, to increase the yield of FcR (Guyre, P. M., et al. (1983) *J. Clin. Invest.* 72:393–397). Five days following the last immunization, the splenocytes were fused with cells of the NSI myeloma line by standard techniques (Kohler, G. and Milstein, C. (1975) *Nature*, 256:495; Ball, E. D., et al., (1982) PNAS 79:5374-5378). Supernatants of the hybrids were screened for their ability to bind to U937 cells by an indirect immunofluorescence assay using a flow cytometer. Chosen hybrids were cloned by limiting dilution, rescreened and expanded either in culture or in ascites fluid. The protein from clone mab 32 was found to be an IgG1 antibody by an immunoblot assay using isotype-specific antisera. IgG of this clone was precipitated from ascites by making the solution 40% in ammonium sulfate. The precipitate was redissolved and dialyzed against 20 mM Tris buffer, pH 8.6. High performance ion exchange chromatography (HPLC) was carried out on a semi-preparative PROTEIN-PAK-5PW (Waters, Milford, Mass.) column. The initial eluting buffer was 20 mM Tris, pH 8.6 delivered by pump A. 20 mM Tris, 0.3 M NaCl, pH 8.6 was delivered by pump B. A sixty minute linear gradient, 0–100% B. at a flow rate of 8 ml/min was used for elution. The main peak corresponding to IgG was pooled. For some experiments the purified IgG was passed over a SepharoseProtein A column to remove traces of IgG2a to less than 0.005%. Pepsin digestion of whole antibody was performed essentially as described by Parham (See Parham, P. (1983) *J. Immunol.* 131: 2895–2902) except that the digestion time was 3 hr and the pH 3.6. F(ab')2 was purified by high performance gel filtration chromatography using a TSK 250 column (Biorad). Fab' was made from F(ab')2 by reducing with 1 mM dithiothreitol for 1 hr at room temperature and alkylating with an excess of iodoacetamide. The Fab' was purified by HPLC using the TSK 250 column.

The preparation of mab 22, mab 44, mab 62 and mab 197 were as above, except that for mabs 22, 44 and 197 the immunogen was IFN-gamma- and dexamethasone activated U937 cells. All procedures and preparations were the same as for mab 32.

The preparation and properties of monoclonal IV3 have been described. See e.g. Looney, R. J. et al. (1986) *J. Immunol.* 136:1641–1647. IV3 was used as supernatant fluid from the culture of cloned cells. Fab fragments of IV3 were prepared as described Looney, R. J. et al. IgG or IgM fractions of murine monoclonal antibodies or myeloma proteins MOPC 141 (IgG2b), anti-Vk3b (IgG2b), P3 (IgG1), AML-2-23 (IgG2b), MY23 (IgG1), RPC5 (IgG2a) and MMA (IgM) were purified from ascites fluids by ion exchange chromatography unless otherwise indicated. In some cases, the supernatant fluid of cloned hybridoma cells was used. Gap8.3 ascites fluid was donated by Dr. Christopher Frantz, Department of Pediatrics, University of Rochester. MY7 was purchased from Coulter, Hialeah, Fla. Leu-M3, an anti-monocyte monoclonal antibody, was obtained from Becton-Dickinson, Mountain View, Calif.

Immune complexes containing human IgG were prepared by incubating tetanus toxin (200 Lf/ml) with Hyper-Tet™ antibody (200 Lf/ml) for 1 hr at 37° C. Insoluble complexes were pelleted by centrifugation at 13,000×g for 1 min, washed once with PBS-K, and resuspended in the original volume of PBS-K. Protein concentration was determined by adding 0.1 M NaOH and measuring absorbance at 280 nm, assuming an extinction coefficient (1%) of 14. Pooled human IgG purified by ion exchange chromatography was covalently linked to Sepharose 4B by a modification of the cyanogen bromide technique (March, S. C. et al., (1974) *Analyt. Biochem.* 60:149–152) at a ratio of 7.6 mg IgG/ml Sepharose. Anti-mIg was linked to CNBr-activated Sepahrose according to the manufacturer's instructions at a ratio of 1mg protein/ml Sepharose. Prior to use the Sepharose adsorbents were washed ×4 with 1% NP40 in PBS containing 5 mM KI.

Cells

Human granulocytes were obtained from the peripheral blood of normal donors by separation from mononuclear cells on Ficoll-Hypaque, sedimentation of erythrocytes using 3% dextran in PBS, and finally hypotonic lysis of residual erythrocytes. Preparations were 98% granulocytes. Mononuclear cells were obtained-by Ficoll-Hypaque separation (Boyum, A. (1968) *Scand. J. Clin. Lab. Invest.* 21:77–83 (Supple. 77)). Cells of the U937, HL60, K562, Daudi, Raji, Molt4, Jurkat and J774 lines were maintained in continuous culture as described. Many of the cell lines used were obtained from the American Type Culture Collection. All cells were washed ×3 in PBS prior to use and were 95% viable when tested by trypan blue exclusion.

Radiolabeling and Affinity Adsorption

Cells were surface radioiodinated by the chloroglycouril method (Fraker, P. J. and Speck, J. C. (1978) *Biochem. Biophys. Research Comm.* 80:849-857). 0.7 ml cells in PBS at 14.3×10⁶/ml were incubated with 1 mCi $^{125}$I for 30 min at 0° C. in a scintillation vial coated with 5 ug chloroglycouril. The reaction was quenched and the cells were washed ×3 with 5 mM KI in PBS. The cells were then lysed in NP40 lysis buffer for 30 min at 0° C. Cell nuclei and other insoluble material were pelleted by centrifugation at 7800×g for 20 min.

SDS-PAGE and Isoelectric Focussing

Sepharose-anti-mIg (25 ul) was sensitized with monoclonal antibodies by incubating for 3 hrs at 4° C. with 100 ul supernatant fluid or Ig purified from ascites fluid (10 ug/ml) and the unbound material washed away ×4 with 0.75 ml BSA/PBS. Portions of labeled cell lysate (50 ul) were incubated for 2 to 12 hr at 0° C. with 25 ul antibody-sensitized Sepharose-anti-mIg. Separate 50 ul portions of lysate were incubated with 25 ul Sepharose-hIgG. The Sepharose conjugates were washed ×7 with 0.75 ml 1% NP40/PBS/KI and in preparation for sizing gel electrophoresis were incubated for 2 min in a boiling water bath with 80 ul Laemmli sample buffer containing 20 mM dithiothrietol instead of 2-mercaptoethanol. The supernatant was acetylated by adding 5 ul 1M iodoacetamide and was analyzed by SDS-PAGE and autoradiography as described: Anderson, C.

L. (1982) *J. Exp. Med.* 156:1794–1805. The molecular weight markers included in all gels were $^{125}$I-bovine serum albumin, $^{125}$I-rabbit muscle actin, phosphorylase B, ovalbumin, carbonic anhydrase, soybean trypsin inhibitor, and lysozyme. For isoelectric focussing, the washed adsorbants were incubated for 15 min with 80 ul of the urea-containing O'Farrell sample buffer and the eluates were electrophoresed on a vertical slab gel prepared as described for the first dimension of the O'Farrell procedure. See O'Farrell, P. H. (1975) *J. Biol. Chem.* 250:4007–4021. The pH gradient was determined by cutting the lateral lanes of the gel into 1 cm sections and incubating each section overnight in 1 ml H$_2$O. The gels were stained and dried, and autoradiographs were prepared using prefogged x-ray film and enhancers at −70° C. as described. See Anderson, C. L. Supra. Densitometric tracings of the p72 band appearing on autoradiographs were enlarged 157% using a photocopier and were cut out with scissors and weighed.

Binding and Inhibition Experiments

A human IgG1 myeloma protein (Arr) and the IgG fraction of mab 32 were radioiodinated by the chloroglycouril method to a specific activity of 1–5 uCi/ug. Preliminary experiments established that equilibrium and saturation were achieved with 4×10$^7$ U937 cells/ml after 2 hr at 0° C. at 0.3 ug/ml for mab 32 and 1.5 ug/ml for hIgG1. Inhibition of the binding of both $^{125}$I-hIgG and $^{125}$I-mab 32 to U93 cells by unlabeled preparations of both hIgG1 and mab 32 was evaluated by incubating the radioligand or radioantibody with cells in the presence of titered amounts of unlabeled antibody or ligand under the above conditions. Cell-bound radioactivity was separated from free by centrifuging triplicate 50 ul portions of the cells suspension through an oil mixture as described. Anderson, C. L. and Abraham, G. N. (1980) *J. Immunol.* 125:2735–2741. Nonspecific binding was measured in replicate samples containing a great excess of ligand (3 mg/ml) or antibody (333 ug/ml). Percent inhibition was calculated as described. Anderson, C. L. and Spiegelberg, H. L. (1981) *J. Immunol.* 126:2470–2473.

Fluorescence and Flow Cytometry

One million cells were incubated for 2 hr at 4° C. in 50 ul of antibody (either mab 32 or IV3 supernatant or 10 ug/ml solutions of purified IgG fractions of ascites fluid) diluted in RPMI 1640 growth medium containing 4 mg/ml hIgG to block nonspecific binding. The cells were washed ×3 in PBS containing 0.1% NaN$_3$, were resuspended and incubated for 2 hr at 4° C. in 50 ul FITC anti-mIgG (TAGO, Burlingame, Calif., or Boehringer-Mannheim, Indianapolis, Ind.), and were washed a final 3 times. Stained cells were analyzed on an Ortho 50H Cytofluorograf flow cytometer using argon lasers at 300 mW or 500 mW power. Green fluorescence was collected through a 525 nm bandpass filter on 10,000–50,000 cells gated for low angle light scatter (to exclude erythrocytes, platelets, dead cells and debris) and 90° C. light scatter (to distinguish monocytes or neutrophils from lymphocytes). See Salzman, G. C. et al. (1975) *Acta Cytol.* 19:374. The 90° light scatter signal characteristic of monocytes was determined by separately staining an aliquot with anti-monocyte antibody Leu-M3. Based on these data, gates for 90° light scatter were adjusted so that the green fluorescence signal of monocytes and lymphocytes in mononuclear cell suspensions could be separately collected. Green fluorescence was collected as a linear signal.

Results

The strategy for the development of monoclonal antibodies against the high affinity 72 kDa FcR had to deal with the observation that two of the four murine IgG subclasses, IgG2a and IgG3, bound with high affinity to this FcR. Thus, any assay for FcR binding would register all antibodies of these two subclasses. Our protocol, therefore, called for immunizing a mouse with partially purified FcR from U937 cells, screening the hybrid supernatants for an Ig capable of binding U937 cells, eliminating from further consideration IgG2a and IgG3 antibodies, and evaluating the remaining antibodies for their capacity to immunoprecipitate 72 kDa surface molecules. (Additional monoclonal antibodies of this specificity (designated mab 22, mab 44 and mab 197) were prepared using whole U937 cells.)

Twenty-nine supernatants from the partially purified FcR immunization contained Ig capable of binding U937 cells. Of these, 12 were of the IgG2a subclass, 1 was IgG3, 7 were IgG1, 2 were IgM, and 7 were either of mixed subclass or could not be typed. The supernatants of the cultures of cloned cells were then evaluated for their ability to bind to a 72 kDa cell surface molecule by an affinity adsorption assay.

Detergent lysates of U937 cells radioiodinated by the chloroglycouril method were incubated, (shown in FIG. 1) from left to right, with Sepharose-antimIg sensitized with purified murine IgG2a myeloma protein RPC5 (lane 1) or with mab 32 (lane 3); with Sepharose-human IgG (lane 4); or with Sepharose-anti-mIg sensitized with mab IV3 (lane 5). The three samples analyzed in the right hand panel were eluted from Sepharose-anti-mIg sensitized with either intact IgG of mab 32(lane 6), with Fab fragments of pooled human IgG (lane 7), or with Fab' fragments of mab 32(lane 8). The immunoadsorbants were washed free of unbound radioactivity and the bound material was eluted in an SDS-containing sample buffer and analyzed by electrophoresis on an SDS-polyacrylamide gel followed by autoradiography. Adjacent lanes not shown but marked on the lateral margins of the autoradiograph contained radio-iodinated bovine albumin (68 kDa) and rabbit muscle actin (43 kDa). Lane 2 contains a mab of the IgG2a subclass.

All of the supernatants containing IgG2a and IgG3 anti-U937 antibodies adsorbed a 72 kDa molecule, as expected. Of the remaining supernatants, one IgG1 (designated mab32) was found capable of adsorbing a 72 kDa molecule and was chosen for further study. Of the remaining 6 IgG1 supernatants, 5 adsorbed a 110 kDa molecule and one adsorbed small amounts of a 72 kDa molecule.

FIG. 1 summarizes these observations. The autoradiograph shows the 72 kDa molecule purified from detergent lysates of radioiodinated U937 cells with mab 32(lane 3). The molecular weight of this molecule as determined on SDS-polyacrylamide gels is indistinguishable from the 72 kDa FcR affinity adsorbed by Sepharose conjugated with ligand capable of interacting with the receptor. Thus, Sepharose-anti-mIg bearing RPC5, a murine IgG2a (lane 1), or Sepharose-human IgG (lane 4) both purify a 72 kDa molecule that has been shown to be the high affinity FcR of U937 cells and human monocytes (See Anderson, C. L., (1982) *J. Exp. Med.* 156:1794–1805). An additional molecule of approximately 40 kDa was adsorbed by Sepharose-human IgG (lane 4). This molecule is a low affinity FcR precipitated by mab IV3 (lane 5) and present on other blood cells as well.

Since mIgG1 antibodies have not been found to bind to the U937 high affinity FcR and since several mIgG1 monoclonal antibodies have failed to immunoprecipitate the 72 kDa FcR (C. L. Anderson, unpublished), it was inferred that mab 32 bound the 72 kDa molecule as an antibody by the Fab portion of the antibody molecule rather than as a ligand by the Fc portion. To confirm this supposition, Fab' fragments of mab 32 were prepared and were tested for their ability to precipitate p72. Lane 8 of FIG. 1 indicates that Sepharose-anti-mIg sensitized with these Fab' fragments of mab 32 purifies the receptor, the Fab fragments of pooled human IgG, do not (lane 7). The 72 kDa molecule purified by the intact IgG of mab 32 is shown in lane 6 for reference.

Although the autoradiograph seen in FIG. 1 shows that the molecule purified by mab 32 is of the same apparent molecular weight as the molecule purified by the ligands, two other methods were utilized to evaluate whether the molecules are identical. First, lysates of radioiodinated U937 cells were precleared with either an affinity adsorbent of mab 32 or with a sham adsorbent (mIgG1 which does not bind or precipitate the FcR). The precleared lysates were then tested for residual p72 by affinity adsorbtion with Sepharose-anti-mIg sensitized with mIgG2a, a ligand which binds this FcR. Radioactive material bound to the adsorbents was analyzed by electrophoresis on SDS-polyacrylamide gels followed by autoradiography and densitometry.

Portions of a lysate of radioiodinated U937 cells were incubated with Sepharose-anti-mig sensitized with several mabs designated as "preclearing adsorbants" in FIG. 2. The affinity adsorbants were centrifuged out of suspension and the supernatants were incubated with a second set of affinity adsorbants designated "final adsorbants". The eluates from the washed set of final adsorbants were processed as described for FIG. 1. A photograph of the set of 72 kDa bands, the only bands appearing on the autoradiograph, is displayed vertically. Densitometric tracings on paper of the autoradiograph bands were cut out and weighed; band density is expressed as mg per band. Percent depletion of p72 by the preclearing adsorbant was calculated by comparing lanes 2 and 3, 1 and 4, 2 and 5, and 1 and 6.

Comparing lanes 1 and 4 of FIG. 2, mab 32 precleared 73% of the p72 subsequently purified by mIgG2a. The reciprocal experiment, preclearing with mIgG2a and then purifying p72 with mab 32, indicates that 89% of p72 was precleared with mIgG2a (lane 3) compared with the mIgG1 sham control (lane 2). Control experiments were performed in which the same reagent (mab or ligand) was used both for pre-clearing and for subsequent purification. These showed the efficiency of preclearing to range from 81% when mab 32 was used (lanes 2 and 5) to 93%. when mIgG2a was used (lanes 1 and 6). We conclude, therefore, that mab 32 binds to the same high affinity 72 kDa FcR purified by ligand affinity adsorption.

Figure 3:
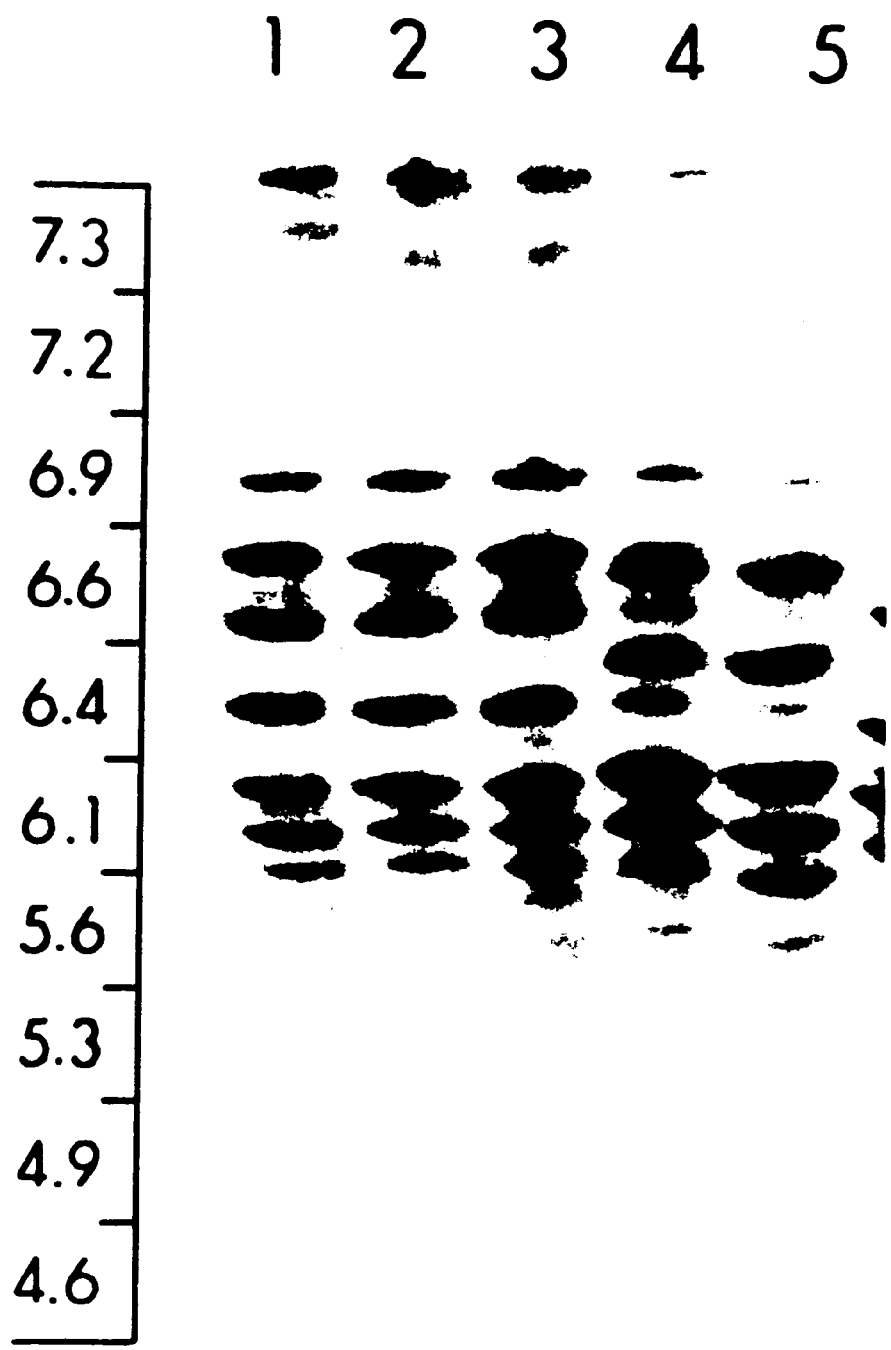
FIG. 3 shows the results of isoelectric focussing of p72 purified either with ligand or with mab 32.

The third method used to test whether the ligand and mab 32 bind the same 72 kDa molecule was isoelectric focusing. FIG. 3 shows the results.

A detergent lysate of radioiodinated U937 cells was incubated with Sepharose-anti-mIg sensitized with either murine IgG2a myeloma RPC5 (lane 1) or mab 32(lane 3); with Sepharose-human IgG (lane 4); or with Sepharose-anti-mIg sensitized with mab IV3 (lane 5). The radioactivity bound to the washed immunoadsorbants was eluted with urea-containing sample buffer and was analyzed by isoelectric focusing and autoradiography. The pH gradient is shown in the left margin. Lane 2 analyzed a mab still under investigation.

An identical pattern of ten distinct bands having isoelectric points ranging from pH 5 to pH 7 was seen in both lanes (FIG. 3, lanes 1 and 3). A similar although subtly distinct pattern of bands was seen in lane 5 analyzing the eluate from the IV3 affinity adsorbent which purified only the 40 kDa FcR. The eluate from Sepharose-human IgG which purifies both the 72 and 40 kDa molecules appears in lane 4 as a composite of the two isoelectric focusing patterns with some of the p72 molecules appearing dimmer than in lanes 1–3, most likely because the p72-ligand bond resists dissociation by urea unlike the p40-ligand bond and unlike antibody-antigen interactions (lanes 1–3). Thus, these data further substantiate the identity of the 72 kDa molecules purified by both FcR ligands and mab 32.

Since IFN-gamma enhances the expression of the high affinity FcR, we used indirect immunofluorescence and flow cytometry to examine the binding of mab 32 to control and IFN-gamma-treated U937 cells. Table 1 shows a 3-fold increment in binding of both mab 32 and a murine IgG2a myeloma protein to IFN-gamma-induced U937 cells. We also determined whether hIgG interferes with the binding of mab 32 to the FcR of U937 cells. As seen in Table 1, hIgG significantly blocked the binding of mIgG2a to the FcR of U937 while the binding of mab 32 was unaffected. This suggests that mab 32 binds to the 72 kDa FcR at a site distinct from the ligand binding site.

TABLE 1

Binding of Mab32 to Control- and IFN Treated U937 Cells

| | Mean Fluorescence Intensity | | | |
|---|---|---|---|---|
| | U937 without IFN | | U937 with IFN | |
| First Antibody | no hIgG | hIgG | no hIgG | hIgG |
| P3(mIgG1) | 39 ± 1 | 46 ± 4 | 55 ± 1 | 52 ± 6 |
| Mab32(mIgG1) | 159 ± 4 | 150 ± 6 | 423 ± 8 | 410 ± 6 |
| RPC5(mIgG2a) | 186 ± 16 | 47 ± 2 | 537 ± 8 | 78 ± 4 |

$5 \times 10^5$ cells from triplicate cultures of U937 cells grown 48 hours with or without 100 IRU/ml IFN were incubated for 2 hours at 4° C. in 60 ul RPMI-1640 containing BSA (2 mg/ml) and 40 ug/ml IgG fraction of the mIgG1 myeloma P3, and mIgG2a myeloma RPC5 (Litton Bionetics) or Mab32. Replicate mixtures contained 4 mg/ml hIgG to block the FcR binding site. After 3 washes (1 ml cold PBS/BSA, 1 mg/ml) the cells were incubated 2 hours at 4° C. with 100 ug/ml FITC anti-mIg (Boehringer-Mannheim), washed with PBS/BSA and fixed in 1% formalin. The cells were analyzed on an Ortho 50H Cytofluorograf using 300 mW excitation at 488 nm. Results are expressed as mean fluorescence intensity ± SD of triplicate cultures. The mean fluorescence intensity of unstained cells (autofluorescence) was 25±2.

Figure 4:
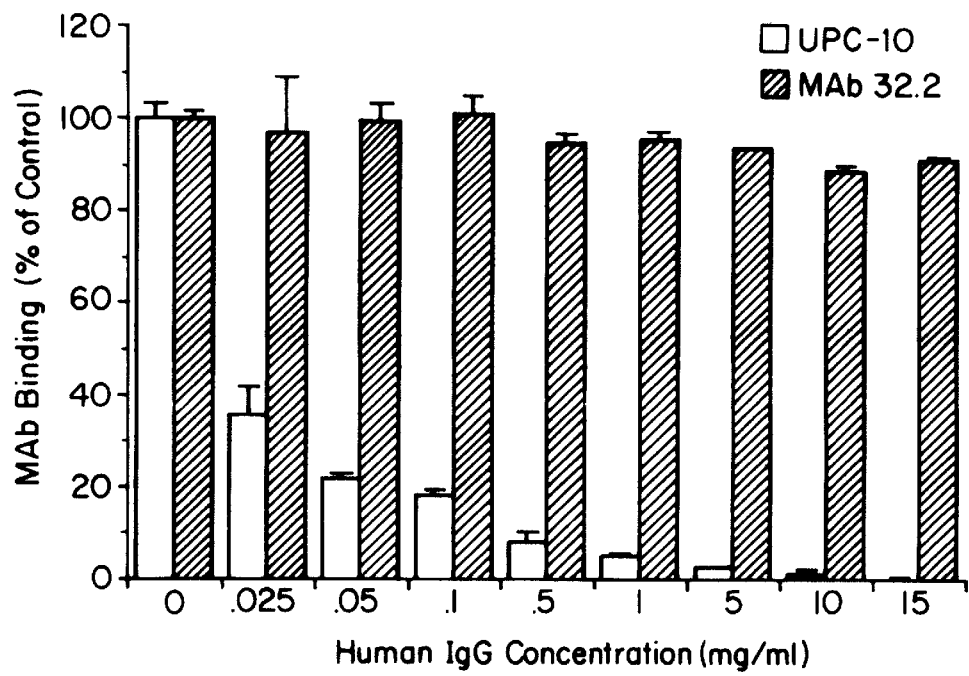
FIG. 4A shows that human IgG does not interfere with the binding of Mab 32 to U937 cells, but blocks, almost completely, the binding of the mouse IgG2a myeloma UPC-10.
FIG. 4b shows that human IgG does not interfer with the binding of Mab 32, 22, 44, 62 and 197 to U937 cells, but blocks almost completely the binding of mouse IgG2a UPC-10; and the increased binding of Mab 32, 22, 44, 62 and 197 to IFN-gamma treated U937 cells.
Figure 4B:
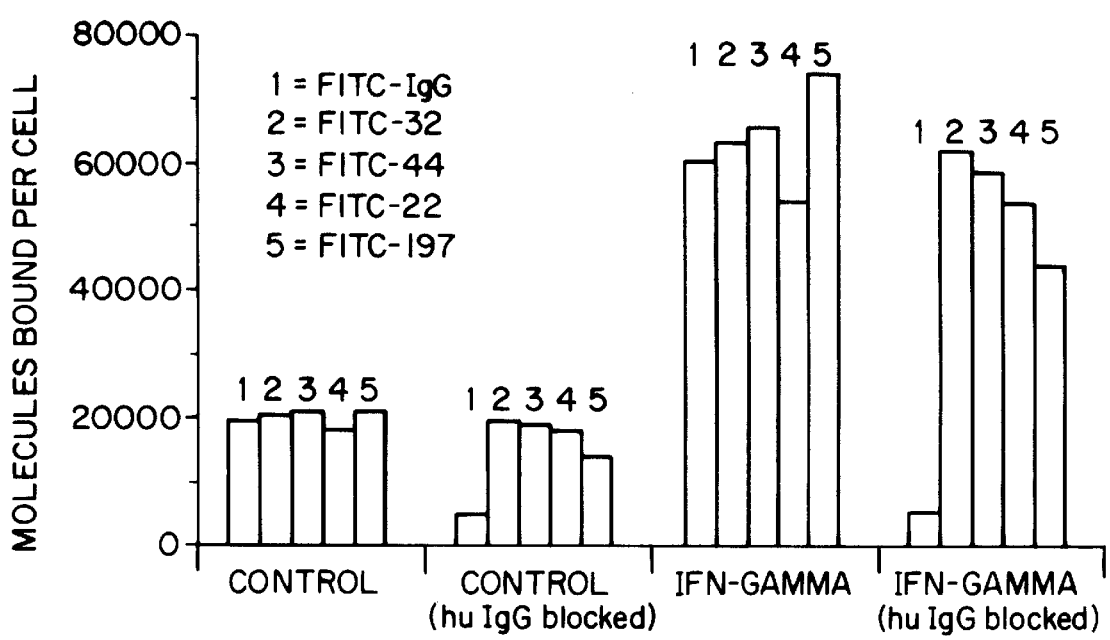

We further quantified the ability of both mab 32 and a ligand, in this case a human IgG1 (hIgG1) myeloma protein (Arr), to inhibit the binding to U937 cells of either $^{125}$I-human IgG1 (Arr) or $^{125}$I-mab 32. FIG. 4a and 4b show the results of these inhibition experiments. Under conditions of saturation and equilibrium, U937 cells were incubated at 4° C. with $^{125}$I-mouse myeloma IgG2a (UPC 10) or $^{125}$I-mab 32 in the presence of varying amounts of unlabeled human IgG1. Bound labeled antibody was separated from free by centrifuging the cells through oil and was quantified by counting the radioactivity associated with the cell pellets. Nonspecific binding measured in the presence of a great excess (100 fold) of unlabeled antibody was subtracted from total binding to give specific binding. Percent inhibition, calculated as described in Materials and Methods, was plotted versus the concentration of inhibitor protein. Non-specific binding was 6–8% of total binding.

As seen in FIGS. 4a and 4b human IgG at concentrations found in human serum (10–15 mg/ml) does not inhibit the binding of mab 32 to Fc receptors on U937 cells. On the other hand, if a ligand which binds to the Fc receptor through the ligand's Fc region is used, serum levels of IgG inhibit the binding by more than 95%. In FIG. 4a and 4b, the mouse myeloma IgG 2a designated UPC-10 was used as the ligand. Identical inhibition by human IgG has also been demonstrated in experiments using human IgG1 as the ligand. We conclude that the binding of mab 32 to cells does not interfere with ligand binding to the FcR binding site and that ligand binding does not inhibit mab 32 binding.

Figure 5A:
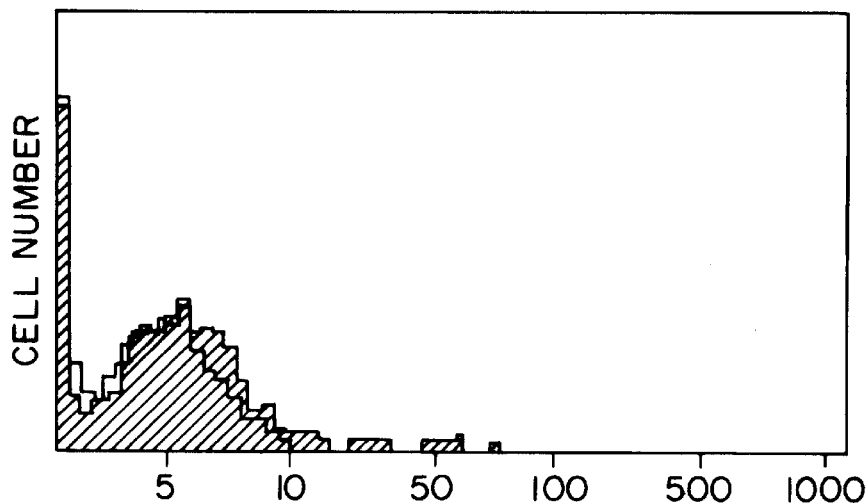
FIGS. 5a, 5b, and 5c show the fluorescence intensity of cells stained with mab 32.
Figure 5B:
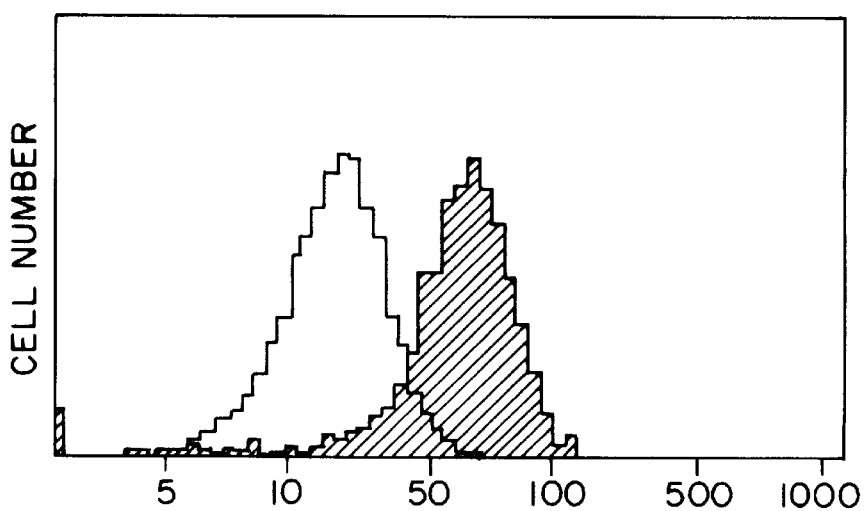
Figure 5C:
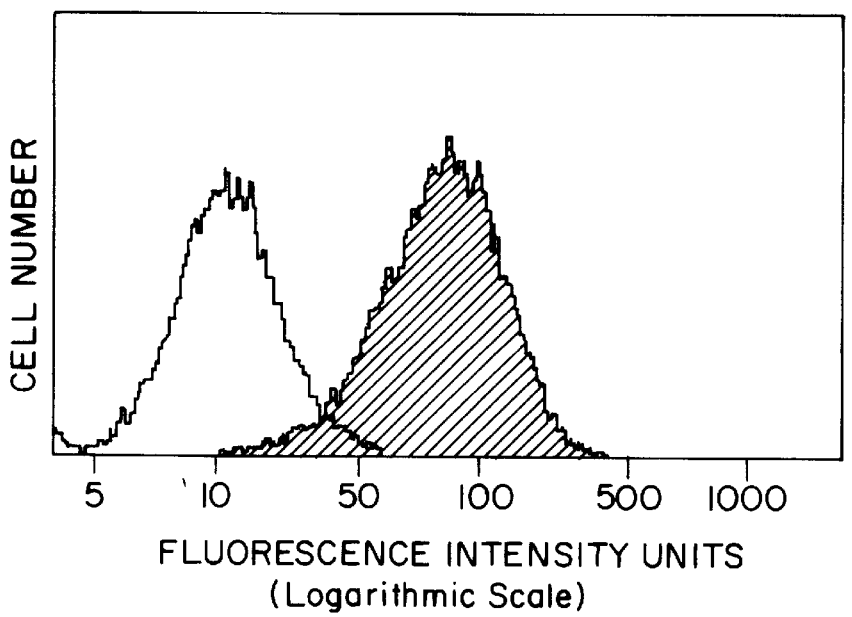

The types of cells which bear the epitope recognized by mab 32 were evaluated by indirect immunofluorescence and flow cytometry and data are presented in Table 2. It is apparent that mab 32 binds to those cells which are known to bear the high affinity IgG FcR, namely U937, HL60, and monocytes. Lymphocytes were negative as were the B cell lines Raji and Daudi, and the T cell lines Molt4 and Jurkat. Some samples of neutrophils showed low level binding of mab 32. FIG. 5a, 5b, and 5c show the fluorescence intensity of cells stained with mab 32. Each panel displays histograms of fluorescence intensity vs cell number for cells stained with mab 32 (shaded area) and murine monoclonal IgG2b control (solid line). Cells shown are: FIG. 5a) lymphocytes, FIG. 5b) monocytes, and FIG. 5c) U937 cells. Monocytes and lymphocytes from a single suspension of blood mononuclear cells were identified by gating on forward and 90° light scatter. FIGS. 5a and 5b are 64 channel histograms (20,000 cells counted). The fluorescence detection gain was set at 1500 to bring the lymphocytes on scale. FIG. 5c is a 256 channel histogram gated on forward angle light scatter (11,000 cells counted). The fluorescence detection gain was set at 1400. The scale of fluorescence intensity units was calibrated by fluorescent microspheres.

TABLE 2

Staining Intensity of Mab32 on Various Cell Types

| | Mean Fluorescence Intensity | | | | |
|---|---|---|---|---|---|
| Cell Type | Mab32 | Control | n | mIgG2a | n |
| U937 | 103 ± 48 | 26 ± 10 | 11 | 92 ± 20 | 6 |
| HL60 | 78 ± 18 | 16 ± 7 | 7 | 80 ± 26 | 3 |
| Monocytes | 113 ± 37 | 29 ± 11 | 8 | | |
| Lymphocytes | 10 ± 2 | 9 ± 3 | 2 | | |
| Neutrophils | 30 ± 4 | 23 ± 3 | 2 | | |
| Daudi | 34 ± 3 | 33 ± 2 | 3 | | |
| Raji | | | | | |
| Molt4 | 18 ± 2 | 18 ± 2 | 3 | | |
| Jurkat | 22 ± 3 | 23 ± 3 | 3 | | |

The specific methods of this experiment are detailed in Methods and Materials. In brief, cells from various lines, peripheral blood mononuclear cells and purified granulocytes were incubated first with either Mab32 or mIgG2a and with control myeloma proteins of the mIgG1 subclass. The washed cells were then incubated with FITC anti-mIg, washed again, and analyzed for fluorescence intensity by flow cytometry. Results are expressed as mean fluorescence intensity (MFI) in arbitrary units ± SD.

As illustrated in FIGS. 5a, 5b, and 5c it should be noted that in spite of some overlap in the fluorescence intensity distribution of cells stained with mab 32 and control antibodies, fluorescence intensity plots of all positive cell types indicated a unimodel distribution with mab 32. This suggests that the entire populations of HL60, U937 cells and mono-cytes, rather than just a major subpopulation, were positive for binding of mab 32.

Discussion

The development of monoclonal antibodies against the high affinity FcR for IgG of human mononuclear phagocytic cells was a particular challenge because two subclasses of murine IgG, IgG2a and IgG3 are ligands capable of binding with high affinity to this receptor (Anderson C. L. and Abraham, G. N. (1980) *J. Immunol.* 125: 2735–2741; Zubeck, M.D. et al (1985) J. Immuol. 135: 12991304). Thus, any assay for mabs capable of binding to the receptor would register as positive all antibodies of these two subclasses. Our strategy was designed to deal with this obstacle, however, and we were successful in obtaining monoclonal antibodies of the IgG1 subclass capable of binding this receptor at sites on the outer surface of the plasma membrane distinct from the ligand binding site. The data supporting this conclusion can be summarized briefly for the prototype antibody mab 32:

First, mab 32 is of the IgG1 subclass. This murine IgG subclass has been found incapable of binding to the high affinity FcR. See e.g. Anderson, C. L. and Abraham, G. N. (1980) *J. Immunol.* 125: 2735. Of the seven IgG1 mabs with anti-U937 activity derived from the fusion described above, four of them adsorbed only a 110 kDa molecule from lysates of surface radioiodinated U937 cells. Thus, adsorption of the 72 kDaFcR is not a general property of IgG1 proteins. (Of the two remaining IgG1 mabs, one adsorbed small amounts of a 72 kDa molecule and the other adsorbed both a 72 kDa and a 110 kDa molecule; these have not yet been further investigated.) Nevertheless, to eliminate the possibility that nab 32 was a variant IgG1 which bound through its Fc region to the FcR, we tested the capacity of Fab' fragments of mab 32 to adsorb the 72 kDa FcR and found that binding occurs independently of the Fc portion of the mab (FIG. 1).

Second, our data show that the 72 kDa molecule adsorbed by mab 32 is the same molecule identified as the high affinity FcR by several criteria previously described. See Anderson, C. L. (1982) *J. Exp. Biol.* 156: 1794. Not only do the molecules appear identical by polyacrylamide gel electrophoresis in SDS (FIG. 1) but the isoelectric focussing patterns of the two molecules are the same as well (FIG. 3). The marked heterogeneity of charge of this molecule has been ascribed to terminal sialic acid residues. The preadsorption experiments shown in FIG. 2 also support the contention that the 72 kDa molecules bound by both ligand and mab 32 are identical. Either ligand or mab 32 is capable of removing the same 72 kDa molecule from detergent solution such that it is no longer available to the other for adsorption.

Third, the data indicate that mab 32 binds to a site on the 72 kDa FcR distinct from the site where ligand binds (FIG. 4a and 4b, Table 1). This observation constitutes direct evidence that in fact mab 32 is not binding to the receptor as a ligand, for if it were it should inhibit ligand binding. The capacity of mab 32 to bind the ligand-occupied FcR should prove useful in a number of circumstances involving detection of the receptor in the presence of ligand. To date this has been impossible.

Fourth, it is quite clear from Table 2 that the only cells which bear the epitope recognized by mab 32 are those which bear the 72 kDa high affinity FcR, namely, monocytes, HL60 cells and U937 cells. This correlation is further evidence that mab 32 is directed against the high affinity FcR. Neutrophils, according to the data of Table 2, are the only other cells capable of binding mab32, but the extent of binding is so low as to be equivocal. Given observations that IFN-gamma induces the expression of this high affinity FcR on neutrophils, it is conceivable that the neutrophils of normal subjects show subtle evidence of induction of this receptor.

Figure 6:
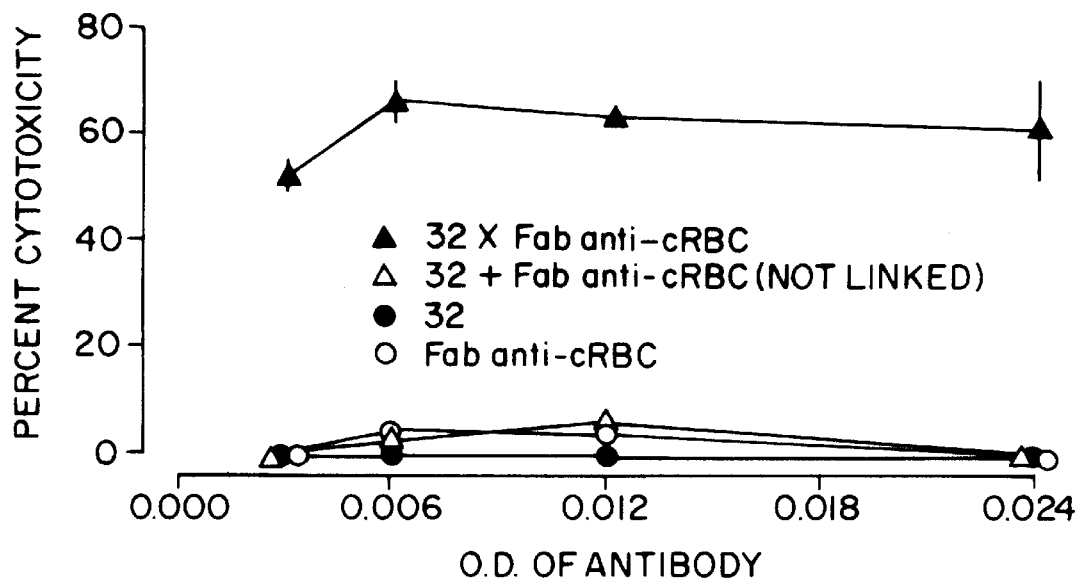
FIG. 6 shows the cytotoxicity of chicken red blood cells (cRBC) by IFN-gamma treated U937 cells mediated by the heteroantibody Mab32×Fab anti-cRBC.
Figure 7:
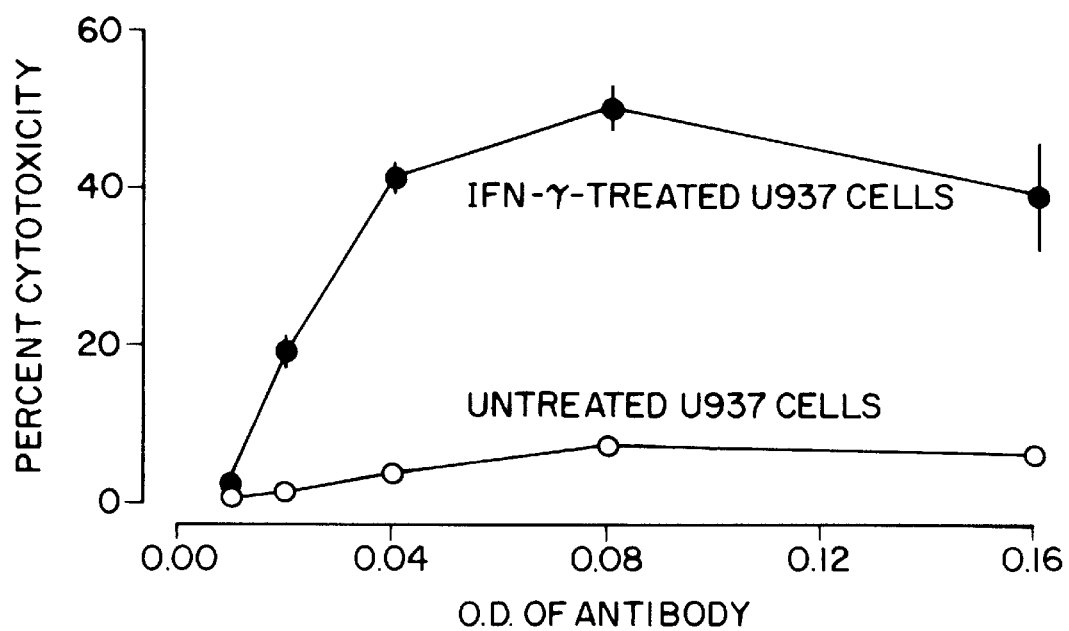
FIG. 7 shows cytotoxicity of CRBC by interferon-gamma treated and untreated U937 cells.
Figure 8:
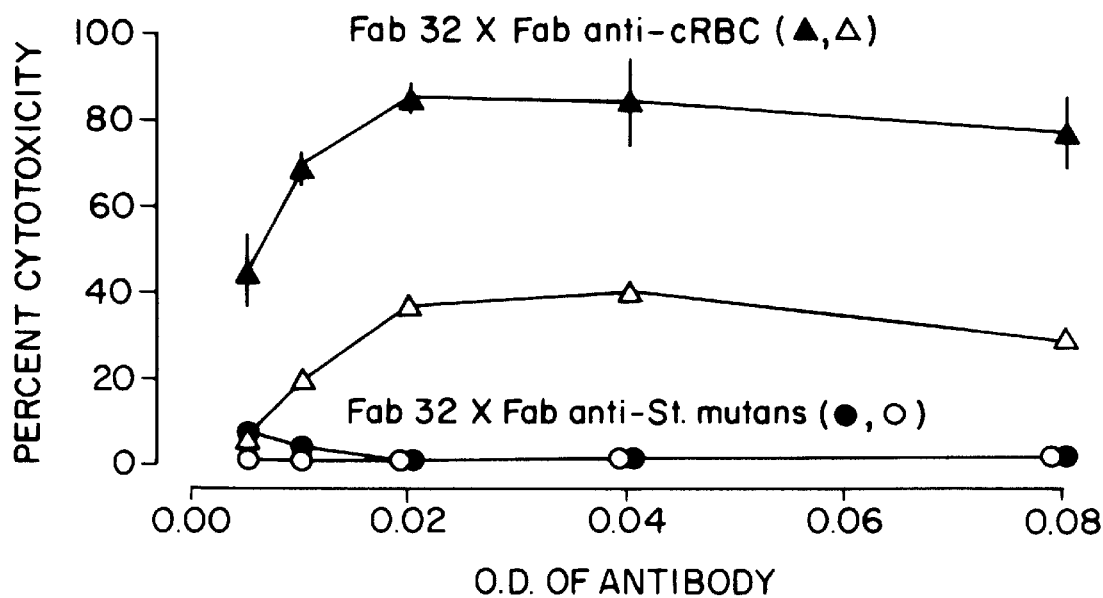
FIG. 8 shows cytotoxicity of chicken cRBC by interferon-gamma treated and untreated human peripheral blood monocytes.
Figure 9:
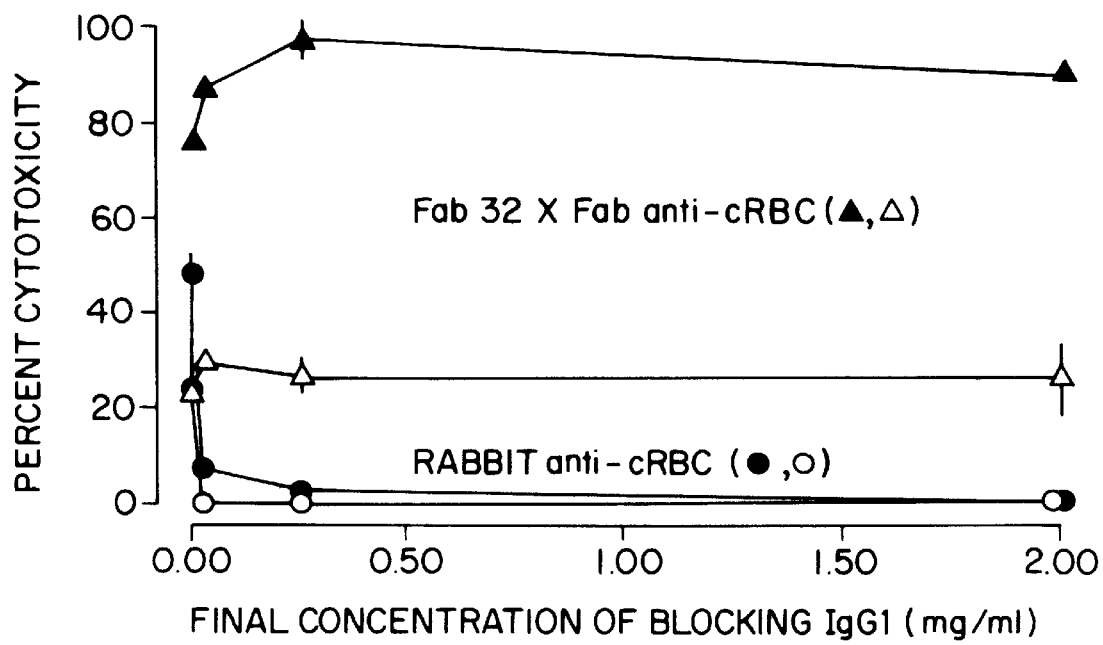
FIG. 9 shows the cytoxicity of cRBC by IFN-gamma treated U937 cells in the presence of the heteroantibody Mab 32×Fab anti-cRBC and human IgG1.
Figure 10:
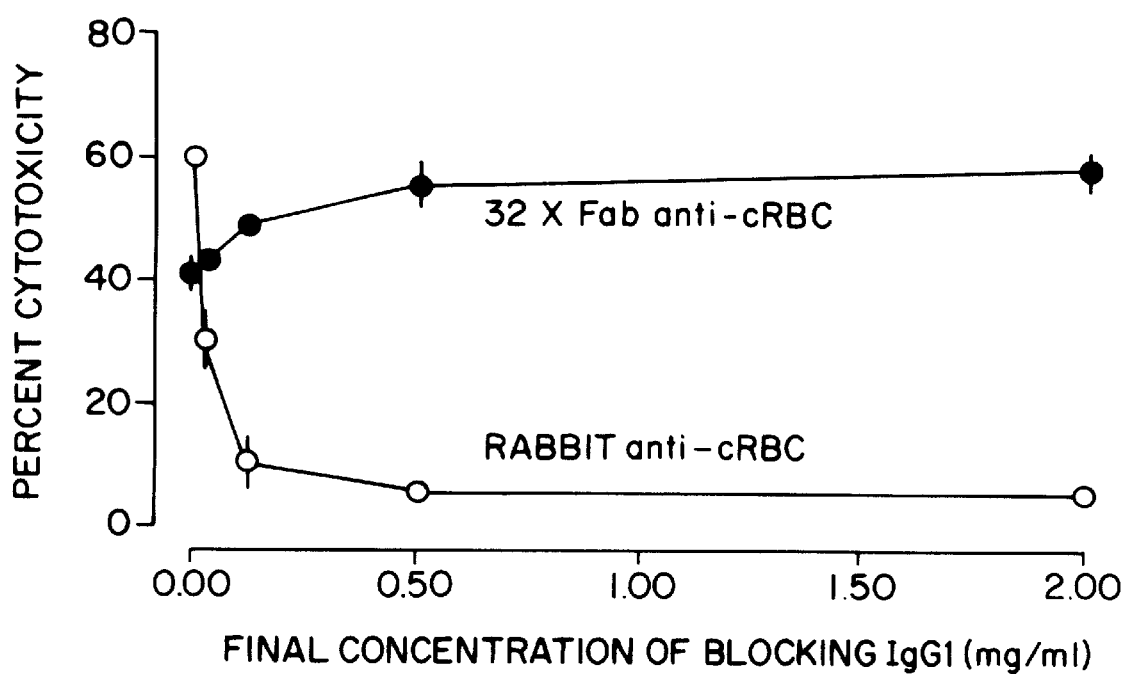
FIG. 10 shows cytotoxicity of cRBC by IFN-gamma treated and untreated human peripheral blood monocytes in the presence of the heteroantibody Mab 32×Fab anti-cRBC and human IgG1.

Anti-Fc Receptor—Anti-Target Cell Antibody Heteroaggregates Mediate Human Monocyte ADCC The IgG1 monoclonal antibody 32.2, raised against the 72 kd monocyte high affinity Fc receptor was used to examine the role of this receptor in ADCC. Whole 32 or its Fab fragments were cross-linked to Fab fragments of rabbit anti-chicken red blood cells (cRBC) using the agent SPDP. The resulting heteroaggregates (32×Fab anti cRBC) mediated monocyte and U937 cytotoxicity against cRBC. See FIG. 6. The covalent association between the anti-Fc receptor and anti-target Fab was found necessary in order for ADCC to occur, since non-cross linked mixtures of 32 and Fab anti-cRBC did not promote ADCC. See FIG. 6. U937 cells did not perform appreciable levels of ADCC unless stimulated with IFN-gamma; but ADCC for these cells was stimulated 3 fold with IFN-gamma. (See FIG. 7) In contrast, unstimulated human, peripheral blood monocytes (PBM) were able to kill cRBC in the presence of 32×Fab anti-CE heteroantibodies, and cytotoxicity was increased by IFN-gamma (FIG. 8). A control heteroantibody of Fab 32×Fab anti-Streptococcus mutans did not stimulate control or IFN-gamma treated monocytes or lyse cRBC targets. See FIG. 8. 32×Fab anti-cRBC promoted cell lysis by U937 cells was not inhibited by high levels of blocking IgG1, while cytotoxicity mediated by rabbit anti-cRBC antibody was readily inhibited by IgG1, both with IFN-gamma treated and untreated U937 cells. See FIG. 9. Fab 32×Fab anti-cRBC-promoted killing by human PBMs, with or without IFN-gamma treatment, was not inhibited by increasing levels of blocking IgG1. Rabbit anti-cRBC antibody promoted killing was quickly inhibited by IgG1 regardless of IFN-gamma induction. See FIG. 10.

In an attempt to define the cell surface determinants on human monocytes that act as trigger molecules for cytotoxicity, hybridoma cells (HC) which produced antibody directed to various human monocyte surface molecules were selected for high expression of surface Ig and used directly as target cells. Hybridoma cells expressing surface Ig directed to the high-affinity FcgR were efficiently killed by human moncytes, whereas hybridoma cells expressing surface Ig directed to other molecules present on the monocyte membrane were not lysed. Thus, FcgRI, when appropriately triggered, specifically initiates monocyte-mediated cytolysis of tumor target cells. (Graziano and Farger. 1987 *J. Immun* 138 945–950).

In previous studies, it has been indicated that IFN-gamma increases both the number of FcgRI molecules per monocyte and the ability of monocytes to mediate ADCC. In the work described here, treatment of monocytes with IFN-gamma did not consistently augment their ability to lyse a hybridoma cell (HC 32.2A) expressing high levels of surface Ig to FcgRI. However, a difference was noted in the susceptibility to monocyte-mediated killing of hybridomas bearing low (HC 32.2C) and high levels of surface Ig anti-FcgRI. Untreated monocytes were able to mediate lysis of both the high (HC 32.2A) and low (HC 32.2A) surface Ig-bearing cells. In contrast, IFN-gamma treated monocytes lysed the two targets equally well. Thus, it appears that IFN-gamma enhances the capability of the monocyte to mediate antibody-dependent killing under conditions where limited antibody is available on the target.

Cytotoxicity of the anti-FcgRI-bearing cell line HC 32.2C was inhibited by soluble 32.2 antibody but not by monomeric human IgG, the natural ligand for the receptor. Although this is not altogether surprising since MAb 32.2 binds to an epitope outside the binding site of FcgRI, it does demonstrate that the ligand binding site of FcgRI need not be occupied in order to trigger human monocytes to kill tumor cells. Furthermore, using mab 32.2 and a second anti-mouse reagent, we have shown that the release of superoxide anion from monocytes requires bridging of FcgRI, suggesting that cross-linking of receptors may also trigger tumor cell cytotoxicity by the monocyte. Certainly target cells coated with antibody and, in the present studies, hybridoma cells expressing multiple anti-FcgRI antibodies per cell would create extensive receptor cross-linking on the monocyte cell surface.

Although in the present study the antibody to FcgRI involved in triggering cytotoxicity was expressed on the surface of the HC that produces it, mab 32.2 may be directed to the surface of other types of tumor cells by linking it to an anti-tumor-specific antibody. The resulting heteroantibody could link tumor cells to monocytes by way of the FcgRI and may trigger lysis of the tumor cell. These reagents would be attractive therapeutic agents, because they would activate and use normal cytotoxic mechanisms present in the host. In addition, because mab 32.2 binds to a region of the FcgRI outside the normal Fc binding site, human IgG or immune complexes would not interfere with its binding in vivo. We have in fact prepared hetero-antibodies that mediate cytotoxicity by monocytes. In particular, reagents composed of the Fab' of mab 32.2 and the Fab' of rabbit anti-chick erythrocyte (CE) antibody mediated killing of CE by monocytes and by IFN-gamma-treated U937 cells. This killing was not blocked by human IgG1. In contrast, heteroantibodies composed of Fab fragments of W6/32 and anti-CE antibodies did not mediate killing of CE by monocytes, again suggesting the-specificity of FcgRI in triggering cytotoxicity.

More importantly, we have prepared hetero-antibodies of mab 32.2 and a monoclonal antibody (SCCL-175) to human small cell carcinoma of the lung (SCCL). We have shown that this hetero-antibody can mediate killing of SCCL cells in vitro by human monocytes (see table 3). Thus, appropriate hetero-antibody can mediate lysis of human tumor cells by human monocytes.

TABLE 3

ADCC OF SCCL CELLS BY
HUMAN MONONUCLEAR CELLS

| Heteroantibody | ug/ml | E/T 40:1 | 60:1 | 80:1 |
|---|---|---|---|---|
| | | % specific cytotoxicity | | |
| SCCL-175 × 32 | 25 | 18 | 24 | 11 |
| | 100 | 31 | 37 | 26 |

The in vivo efficacy of hetero-antibodies composed of mab 32.2 and anti-tumor antibodies may be enhanced by the use of physiologic mediators such as IFN-gamma or calcitriol.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating a disease, comprising administering to a patient afflicted with the disease a therapeutically effective amount of a bifunctional antibody or a heteroantibody comprising:
   an antigen binding region specific for a high affinity Fc receptor for IgG, the binding of which to human Fc receptor is not blocked by human IgG; and
   an antigen binding region specific for a target epitope.

2. The method of claim 1, wherein the disease is selected from the group consisting of a cancer and infectious disease.

3. A method of directing an effector cell to a target cell, comprising contacting the effector cell with a bifunctional antibody or a heteroantibody comprising:

an antigen binding region specific for a high affinity Fc receptor for IgG, the binding of which to human F receptor is not blocked by human IgG; and an antigen binding region specific for a target cell, wherein the contacting step occurs in the presence of the target cell such that the effector cell is directed to the target cell.

4. The method of claim 3, wherein the target cell is a tumor cell.

5. The method of claim 3, wherein the effector cell is selected from the group consisting of leukocytes, monocytes, neutrophils, natural killer cells and eosinophils.

6. The method of claim 3, wherein the effector cell is treated with interferon-gamma before contacting said bifunctional antibody or heteroantibody.

* * * * *

UNITED STATES PATENT AND TRADEMARK OFFICE
CERTIFICATE OF CORRECTION

PATENT NO. : 6,096,311
DATED : August 1, 2000
INVENTOR(S) : Fanger *et al.*

It is certified that error appears in the above-identified patent and that said Letters Patent is hereby corrected as shown below:

In field [54] please delete "Methods for Use of Monoclonal Antibodies Specific for the High Affinity FC Receptor for Immunoglobulin G" and insert -- Antibodies Specific for the High Affinity Fc Receptor for Immunoglobulin G on Human Mononuclear Phagocytes --.

Signed and Sealed this

Twenty-fourth Day of April, 2001

Attest:

NICHOLAS P. GODICI

*Attesting Officer*  *Acting Director of the United States Patent and Trademark Office*